US005866552A

United States Patent [19]
Wilson et al.

[11] Patent Number: 5,866,552
[45] Date of Patent: *Feb. 2, 1999

[54] METHOD FOR EXPRESSING A GENE IN THE ABSENCE OF AN IMMUNE RESPONSE

[75] Inventors: James M. Wilson, Gladwyne; Krishna J. Fisher, Philadelphia, both of Pa.

[73] Assignee: The Trustees of the University of Pennsylvania, Philadelphia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 708,188

[22] Filed: Sep. 6, 1996

[51] Int. Cl.⁶ .......................... C12N 15/63; A01N 43/04; A61K 31/70
[52] U.S. Cl. .................. 514/44; 435/172.3; 435/320.1; 435/325; 435/69.1; 424/93.21
[58] Field of Search ................. 514/2, 44; 435/320.1, 435/172.3, 240.1, 240.2, 48, 325, 69.1; 424/93.21

[56] References Cited

U.S. PATENT DOCUMENTS

| 5,139,941 | 8/1992 | Muzyczka | 435/172.3 |
|---|---|---|---|
| 5,173,414 | 12/1992 | Lebkowski | 435/172.3 |
| 5,252,479 | 10/1993 | Srivastava | 435/235.1 |
| 5,354,678 | 10/1994 | Lebkowski | 435/172.3 |
| 5,436,146 | 7/1995 | Shenk | 435/172.3 |
| 5,474,935 | 12/1995 | Chatterjee | 435/320.1 |
| 5,478,745 | 12/1995 | Samulski | 435/320.1 |
| 5,753,500 | 5/1998 | Shenk et al. | 435/320.1 |

FOREIGN PATENT DOCUMENTS

| 27902/92 | 4/1993 | Australia . |
| WO91/18088 | 11/1991 | WIPO . |
| WO93/24641 | 12/1993 | WIPO . |
| 9413788 | 6/1994 | WIPO . |
| WO94/20517 | 9/1994 | WIPO . |
| WO95/06743 | 3/1995 | WIPO . |
| WO95/07995 | 3/1995 | WIPO . |
| WO95/13392 | 5/1995 | WIPO . |
| WO95/14771 | 6/1995 | WIPO . |
| WO95/20671 | 8/1995 | WIPO . |
| WO95/23867 | 9/1995 | WIPO . |
| WO95/28493 | 10/1995 | WIPO . |
| WO95/33824 | 12/1995 | WIPO . |
| WO95/34670 | 12/1995 | WIPO . |
| WO96/00587 | 1/1996 | WIPO . |
| WO96/12010 | 4/1996 | WIPO . |
| WO96/17947 | 6/1996 | WIPO . |
| WO96/18727 | 6/1996 | WIPO . |
| WO 96/40272 | 12/1996 | WIPO . |
| WO 97/26336 | 7/1997 | WIPO . |
| WO 97/26337 | 8/1997 | WIPO . |

OTHER PUBLICATIONS

D. Coovert et al, "Gene Therapy for Muscle Diseases", *Current Opinion in Neurology*, 7:463–470 (1994).
R. Herzog et al, "Stable Gene Transfer and Expression of Human Blood Coagulation Factor IX After Intramuscular Injection of Recombinant Adeno–Associated Virus", *Proc. Natl. Acad. Sci. USA*, 94:5804–5809 (May 1997).
K. Fisher et al, "Recombinant Adeno–Associated Virus for Muscle Directed Gene Therapy", *Nature Medicine*, 3(3):306–312 (Mar. 1997).
P. Kessler et al, "Gene Delivery to Skeletal Muscle Results in Sustained Expression and Systemic Delivery of a Therapeutic Protein", *Proc. Natl. Acad. Sci. USA*, 93:14082–14087 (Nov. 1996).
D. Russell et al, "Adeno–Associated Virus Vectors Preferentially Transduce Cells in S Phase", *Proc. Natl. Acad. Sci. USA*, 91:8915–8919 (Sep. 1994).
J. Wolff et al, "Direct Gene Transfer into Mouse Muscle in Vivo", *Science*, 247:1465–1468 (Mar. 23, 1990).
H. Blau et al, "Localization of Muscle Gene Products in Nuclear Domains: Does this Constitute a Problem for Myoblast Therapy?", *Adv. Exp. Med. Biol.*, 280:167–172 (1990).
N. Muzyczka, "Use of Adeno–Associated Virus as a General Transduction Vector for Mammalian Cells", *Curr. Topics Microbiol. Immunol.*, 158:97–129 (1992).
R. Samulski et al, "Targeted Integration of Adeno–Associated Virus (AAV) into Human Chromosome 19", *EMBO J.*, 10(12):3941–3950 (1991).
R. Kotin, "Prospects for the Use of Adeno–Associated Virus as a Vector for Human Gene Therapy", *Human Gene Therapy*, 5:793–801 (1994) [Kotin I].
R. Kotin et al, "Site–Specific Integration by Adeno–Associated Virus", *Proc. Natl. Acad. Sci. USA*, 87:2211–2215 (Mar. 1990) [Kotin II].
K. Fisher et al, "Transduction with Recombinant Adeno–Associated Virus for Gene Therapy is Limited by Leading–Strand Synthesis", *J. Virol.*, 70(1):520–532 (Jan. 1996).
C. Hodgson, "Advances in Vector Systems for Gene Therapy", *Exp. Opin. Ther. Patents*, 5(5):459–468 (1995).
R. Samulski et al, "Helper–Free Stocks of Recombinant Adeno–Associated Viruses: Normal Integration Does not Require Viral Gene Expression", *J. Virol.*, 63(9):3822–3828 (Sep. 1989).
M. Weitzman et al, "Recruitment of Wild–Type and Recombinant Adeno–Associated Virus into Adenovirus Replication Centers", *J. Virol.*, 70(3):1845–1854 (Mar. 1996).
S. Goodman et al, "Recombinant Adeno–Associated Virus–Mediated Gene Transfer into Hematopoietic Progenitor Cells", *Blood*, 84(5):1492–1500 (Sep. 1994).
B. Yakobson et al, "Replication of Adeno–Associated Virus in Synchronized Cells without the Addition of a Helper Virus", *J. Virol.*, 61(4):972–981 (Apr. 1987).
E. Kremer et al, "Adenovirus and Adeno–Associated Virus Mediated Gene Transfer", *British Medical Bulletin*, 51(1):31–44 (1995).
E. Raz et al, "Systemic Immunological Effects of Cytokine Genes Injected into Skeletal Muscle", *Proc. Natl. Acad. Sci. USA*, 90:4523–4527 (May 1993).

(List continued on next page.)

*Primary Examiner*—Christopher F. Low
*Assistant Examiner*—Jill D. Schmuck
*Attorney, Agent, or Firm*—Howson and Howson

[57] ABSTRACT

A method of gene transfer involving administering a recombinant adeno-associated virus (AAV) bearing the desired gene into the muscle of the animal is described.

4 Claims, 10 Drawing Shee

OTHER PUBLICATIONS

Xaio et al. J. of Virol. 70(11):8098–8108, Nov. 1996.
Xiao et al. Adv. Drug Del. Rev. 12:201–215, 1993.
March et al. Clin. Res. 40(2) 358A, 1992.
Kaplitt et al Nature Genetics 8:148–153, Oct. 1994.
Einerhand et al. Gene Therapy 2(5):336–343, Jul. 1995.
Bartlett et al. Amer. J. Human Genetics 57.supp 4#A235, Oct. 1995.
LaFont Lancet. 346:1442–1443, 1995.
Orkin et al. Report and Recomendations . . . Gene Therapy. NIHPress. Dec. 7, 1995. pp. 1–40.
Miller et al. FASEB. vol. 9 :190–199, Feb. 1995.
Marshall. Science.269:1050–1055, Aug. 1995.
Culver et al. TIG. 10(5):174–178, May 1994.
Hodgson. Exp Opin Ther. Patents. 5(5):459–468, 1995. ts

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 10398 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:1:

```
GAATTCGCTA  GCATCATCAA  TAATATACCT  TATTTTGGAT  TGAAGCCAAT  ATGATAATGA      60

GGGGGTGGAG  TTTGTGACGT  GGCGCGGGGC  GTGGGAACGG  GGCGGGTGAC  GTAGTAGTGT     120

GGCGGAAGTG  TGATGTTGCA  AGTGTGGCGG  AACACATGTA  AGCGACGGAT  GTGGCAAAAG     180

TGACGTTTTT  GGTGTGCGCC  GGTGTACACA  GGAAGTGACA  ATTTTCGCGC  GGTTTTAGGC     240

GGATGTTGTA  GTAAATTTGG  GCGTAACCGA  GTAAGATTTG  GCCATTTTCG  CGGGAAAACT     300

GAATAAGAGG  AAGTGAAATC  TGAATAATTT  TGTGTTACTC  ATAGCGCGTA  ATATTTGTCT     360

AGGGAGATCT  GCTGCGCGCT  CGCTCGCTCA  CTGAGGCCGC  CCGGGCAAAG  CCCGGGCGTC     420
```

-continued

```
GGGCGACCTT TGGTCGCCCG GCCTCAGTGA GCGAGCGAGC GCGCAGAGAG GGAGTGGCCA      480
ACTCCATCAC TAGGGGTTCC TTGTAGTTAA TGATTAACCC GCCATGCTAC TTATCTACAA      540
TTCGAGCTTG CATGCCTGCA GGTCGTTACA TAACTTACGG TAAATGGCCC GCCTGGCTGA      600
CCGCCCAACG ACCCCCGCCC ATTGACGTCA ATAATGACGT ATGTTCCCAT AGTAACGCCA      660
ATAGGGACTT TCCATTGACG TCAATGGGTG GAGTATTTAC GGTAAACTGC CCACTTGGCA      720
GTACATCAAG TGTATCATAT GCCAAGTACG CCCCCTATTG ACGTCAATGA CGGTAAATGG      780
CCCGCCTGGC ATTATGCCCA GTACATGACC TTATGGGACT TTCCTACTTG GCAGTACATC      840
TACGTATTAG TCATCGCTAT TACCATGGTG ATGCGGTTTT GGCAGTACAT CAATGGGCGT      900
GGATAGCGGT TTGACTCACG GGATTTCCA AGTCTCCACC CCATTGACGT CAATGGGAGT      960
TTGTTTTGGC ACCAAAATCA ACGGGACTTT CCAAAATGTC GTAACAACTC CGCCCCATTG     1020
ACGCAAATGG GCGGTAGGCG TGTACGGTGG GAGGTCTATA TAAGCAGAGC TCGTTTAGTG     1080
AACCGTCAGA TCGCCTGGAG ACGCCATCCA CGCTGTTTTG ACCTCCATAG AAGACACCGG     1140
GACCGATCCA GCCTCCGGAC TCTAGAGGAT CCGGTACTCG AGGAACTGAA AAACCAGAAA     1200
GTTAACTGGT AAGTTTAGTC TTTTTGTCTT TTATTTCAGG TCCCGGATCC GGTGGTGGTG     1260
CAAATCAAAG AACTGCTCCT CAGTGGATGT TGCCTTTACT TCTAGGCCTG TACGGAAGTG     1320
TTACTTCTGC TCTAAAAGCT GCGGAATTGT ACCCGCGGCC GCAATTCCG GGGATCGAAA     1380
GAGCCTGCTA AAGCAAAAAA GAAGTCACCA TGTCGTTTAC TTTGACCAAC AAGAACGTGA     1440
TTTTCGTTGC CGGTCTGGGA GGCATTGGTC TGGACACCAG CAAGGAGCTG CTCAAGCGCG     1500
ATCCCGTCGT TTACAACGT CGTGACTGGG AAAACCCTGG CGTTACCCAA CTTAATCGCC     1560
TTGCAGCACA TCCCCCTTTC GCCAGCTGGC GTAATAGCGA AGAGGCCCGC ACCGATCGCC     1620
CTTCCCAACA GTTGCGCAGC CTGAATGGCG AATGGCGCTT TGCCTGGTTT CCGGCACCAG     1680
AAGCGGTGCC GGAAAGCTGG CTGGAGTGCG ATCTTCCTGA GGCCGATACT GTCGTCGTCC     1740
CCTCAAACTG GCAGATGCAC GGTTACGATG CGCCCATCTA CACCAACGTA ACCTATCCCA     1800
TTACGGTCAA TCCGCCGTTT GTTCCCACGG AGAATCCGAC GGGTTGTTAC TCGCTCACAT     1860
TTAATGTTGA TGAAAGCTGG CTACAGGAAG GCCAGACGCG AATTATTTTT GATGGCGTTA     1920
ACTCGGCGTT TCATCTGTGG TGCAACGGGC GCTGGGTCGG TTACGGCCAG ACAGTCGTT     1980
TGCCGTCTGA ATTTGACCTG AGCGCATTTT TACGCGCCGG AGAAAACCGC CTCGCGGTGA     2040
TGGTGCTGCG TTGGAGTGAC GGCAGTTATC TGGAAGATCA GGATATGTGG CGGATGAGCG     2100
GCATTTTCCG TGACGTCTCG TTGCTGCATA AACCGACTAC ACAAATCAGC GATTTCCATG     2160
TTGCCACTCG CTTTAATGAT GATTTCAGCC GCGCTGTACT GGAGGCTGAA GTTCAGATGT     2220
GCGGCGAGTT GCGTGACTAC CTACGGGTAA CAGTTTCTTT ATGGCAGGGT GAAACGCAGG     2280
TCGCCAGCGG CACCGCGCCT TTCGGCGGTG AAATTATCGA TGAGCGTGGT GGTTATGCCG     2340
ATCGCGTCAC ACTACGTCTG AACGTCGAAA ACCCGAAACT GTGGAGCGCC GAAATCCCGA     2400
ATCTCTATCG TGCGGTGGTT GAACTGCACA CCGCCGACGG CACGCTGATT GAAGCAGAAG     2460
CCTGCGATGT CGGTTTCCGC GAGGTGCGGA TTGAAAATGG TCTGCTGCTG CTGAACGGCA     2520
AGCCGTTGCT GATTCGAGGC GTTAACCGTC ACGAGCATCA TCCTCTGCAT GGTCAGGTCA     2580
TGGATGAGCA GACGATGGTG CAGGATATCC TGCTGATGAA GCAGAACAAC TTTAACGCCG     2640
TGCGCTGTTC GCATTATCCG AACCATCCGC TGTGGTACAC GCTGTGCGAC CGCTACGGCC     2700
TGTATGTGGT GGATGAAGCC AATATTGAAA CCCACGGCAT GGTGCCAATG AATCGTCTGA     2760
CCGATGATCC GCGCTGGCTA CCGGCGATGA GCGAACGCGT AACGCGAATG GTGCAGCGCG     2820
```

| | | | | | | |
|---|---|---|---|---|---|---|
| ATCGTAATCA | CCCGAGTGTG | ATCATCTGGT | CGCTGGGGAA | TGAATCAGGC | CACGGCGCTA | 2880 |
| ATCACGACGC | GCTGTATCGC | TGGATCAAAT | CTGTCGATCC | TTCCCGCCCG | GTGCAGTATG | 2940 |
| AAGGCGGCGG | AGCCGACACC | ACGGCCACCG | ATATTATTTG | CCCGATGTAC | GCGCGCGTGG | 3000 |
| ATGAAGACCA | GCCCTTCCCG | GCTGTGCCGA | AATGGTCCAT | CAAAAAATGG | CTTTCGCTAC | 3060 |
| CTGGAGAGAC | GCGCCCGCTG | ATCCTTTGCG | AATACGCCCA | CGCGATGGGT | AACAGTCTTG | 3120 |
| GCGGTTTCGC | TAAATACTGG | CAGGCGTTTC | GTCAGTATCC | CCGTTTACAG | GGCGGCTTCG | 3180 |
| TCTGGGACTG | GGTGGATCAG | TCGCTGATTA | AATATGATGA | AAACGGCAAC | CCGTGGTCGG | 3240 |
| CTTACGGCGG | TGATTTTGGC | GATACGCCGA | ACGATCGCCA | GTTCTGTATG | AACGGTCTGG | 3300 |
| TCTTTGCCGA | CCGCACGCCG | CATCCAGCGC | TGACGGAAGC | AAAACACCAG | CAGCAGTTTT | 3360 |
| TCCAGTTCCG | TTTATCCGGG | CAAACCATCG | AAGTGACCAG | CGAATACCTG | TTCCGTCATA | 3420 |
| GCGATAACGA | GCTCCTGCAC | TGGATGGTGG | CGCTGGATGG | TAAGCCGCTG | GCAAGCGGTG | 3480 |
| AAGTGCCTCT | GGATGTCGCT | CCACAAGGTA | AACAGTTGAT | TGAACTGCCT | GAACTACCGC | 3540 |
| AGCCGGAGAG | CGCCGGGCAA | CTCTGGCTCA | CAGTACGCGT | AGTGCAACCG | AACGCGACCG | 3600 |
| CATGGTCAGA | AGCCGGGCAC | ATCAGCGCCT | GGCAGCAGTG | GCGTCTGGCG | GAAAACCTCA | 3660 |
| GTGTGACGCT | CCCCGCCGCG | TCCCACGCCA | TCCCGCATCT | GACCACCAGC | GAAATGGATT | 3720 |
| TTTGCATCGA | GCTGGGTAAT | AAGCGTTGGC | AATTTAACCG | CCAGTCAGGC | TTTCTTTCAC | 3780 |
| AGATGTGGAT | TGGCGATAAA | AAACAACTGC | TGACGCCGCT | GCGCGATCAG | TTCACCCGTG | 3840 |
| CACCGCTGGA | TAACGACATT | GGCGTAAGTG | AAGCGACCCG | CATTGACCCT | AACGCCTGGG | 3900 |
| TCGAACGCTG | GAAGGCGGCG | GGCCATTACC | AGGCCGAAGC | AGCGTTGTTG | CAGTGCACGG | 3960 |
| CAGATACACT | TGCTGATGCG | GTGCTGATTA | CGACCGCTCA | CGCGTGGCAG | CATCAGGGGA | 4020 |
| AAACCTTATT | TATCAGCCGG | AAAACCTACC | GGATTGATGG | TAGTGGTCAA | ATGGCGATTA | 4080 |
| CCGTTGATGT | TGAAGTGGCG | AGCGATACAC | CGCATCCGGC | GCGGATTGGC | CTGAACTGCC | 4140 |
| AGCTGGCGCA | GGTAGCAGAG | CGGGTAAACT | GGCTCGGATT | AGGGCCGCAA | GAAAACTATC | 4200 |
| CCGACCGCCT | TACTGCCGCC | TGTTTTGACC | GCTGGGATCT | GCCATTGTCA | GACATGTATA | 4260 |
| CCCCGTACGT | CTTCCCGAGC | GAAAACGGTC | TGCGCTGCGG | GACGCGCGAA | TTGAATTATG | 4320 |
| GCCCACACCA | GTGGCGCGGC | GACTTCCAGT | TCAACATCAG | CCGCTACAGT | CAACAGCAAC | 4380 |
| TGATGGAAAC | CAGCCATCGC | CATCTGCTGC | ACGCGGAAGA | AGGCACATGG | CTGAATATCG | 4440 |
| ACGGTTTCCA | TATGGGGATT | GGTGGCGACG | ACTCCTGGAG | CCCGTCAGTA | TCGGCGGAAT | 4500 |
| TACAGCTGAG | CGCCGGTCGC | TACCATTACC | AGTTGGTCTG | GTGTCAAAAA | TAATAATAAC | 4560 |
| CGGGCAGGCC | ATGTCTGCCC | GTATTTCGCG | TAAGGAAATC | CATTATGTAC | TATTTAAAAA | 4620 |
| ACACAAACTT | TTGGATGTTC | GGTTTATTCT | TTTTCTTTTA | CTTTTTTATC | ATGGGAGCCT | 4680 |
| ACTTCCCGTT | TTTCCCGATT | TGGCTACATG | ACATCAACCA | TATCAGCAAA | AGTGATACGG | 4740 |
| GTATTATTTT | TGCCGCTATT | TCTCTGTTCT | CGCTATTATT | CCAACCGCTG | TTTGGTCTGC | 4800 |
| TTTCTGACAA | ACTCGGCCTC | GACTCTAGGC | GGCCGCGGGG | ATCCAGACAT | GATAAGATAC | 4860 |
| ATTGATGAGT | TTGGACAAAC | CACAACTAGA | ATGCAGTGAA | AAAATGCTT | TATTTGTGAA | 4920 |
| ATTTGTGATG | CTATTGCTTT | ATTTGTAACC | ATTATAAGCT | GCAATAAACA | AGTTAACAAC | 4980 |
| AACAATTGCA | TTCATTTTAT | GTTTCAGGTT | CAGGGGGAGG | TGTGGGAGGT | TTTTTCGGAT | 5040 |
| CCTCTAGAGT | CGAGTAGATA | AGTAGCATGG | CGGGTTAATC | ATTAACTACA | AGGAACCCCT | 5100 |
| AGTGATGGAG | TTGGCCACTC | CCTCTCTGCG | CGCTCGCTCG | CTCACTGAGG | CCGGGCGACC | 5160 |
| AAAGGTCGCC | CGACGCCCGG | GCTTTGCCCG | GCGGCCTCA | GTGAGCGAGC | GAGCGCGCAG | 5220 |

| | | | | | | |
|---|---|---|---|---|---|---|
| CAGATCTGGA | AGGTGCTGAG | GTACGATGAG | ACCCGCACCA | GGTGCAGACC | CTGCGAGTGT | 5280 |
| GGCGGTAAAC | ATATTAGGAA | CCAGCCTGTG | ATGCTGGATG | TGACCGAGGA | GCTGAGGCCC | 5340 |
| GATCACTTGG | TGCTGGCCTG | CACCCGCGCT | GAGTTTGGCT | CTAGCGATGA | AGATACAGAT | 5400 |
| TGAGGTACTG | AAATGTGTGG | GCGTGGCTTA | AGGGTGGGAA | AGAATATATA | AGGTGGGGGT | 5460 |
| CTTATGTAGT | TTTGTATCTG | TTTTGCAGCA | GCCGCCGCCG | CCATGAGCAC | CAACTCGTTT | 5520 |
| GATGGAAGCA | TTGTGAGCTC | ATATTTGACA | ACGCGCATGC | CCCCATGGGC | CGGGGTGCGT | 5580 |
| CAGAATGTGA | TGGGCTCCAG | CATTGATGGT | CGCCCGTCC | TGCCCGCAAA | CTCTACTACC | 5640 |
| TTGACCTACG | AGACCGTGTC | TGGAACGCCG | TTGGAGACTG | CAGCCTCCGC | CGCCGCTTCA | 5700 |
| GCCGCTGCAG | CCACCGCCCG | CGGGATTGTG | ACTGACTTTG | CTTTCCTGAG | CCCGCTTGCA | 5760 |
| AGCAGTGCAG | CTTCCCGTTC | ATCCGCCCGC | GATGACAAGT | TGACGGCTCT | TTTGGCACAA | 5820 |
| TTGGATTCTT | TGACCCGGGA | ACTTAATGTC | GTTCTCAGC | AGCTGTTGGA | TCTGCGCCAG | 5880 |
| CAGGTTTCTG | CCCTGAAGGC | TTCCTCCCCT | CCCAATGCGG | TTTAAAACAT | AAATAAAAAA | 5940 |
| CCAGACTCTG | TTTGGATTTG | GATCAAGCAA | GTGTCTTGCT | GTCTTTATTT | AGGGGTTTTG | 6000 |
| CGCGCGCGGT | AGGCCCGGGA | CCAGCGGTCT | CGGTCGTTGA | GGGTCCTGTG | TATTTTTTCC | 6060 |
| AGGACGTGGT | AAAGGTGACT | CTGGATGTTC | AGATACATGG | GCATAAGCCC | GTCTCTGGGG | 6120 |
| TGGAGGTAGC | ACCACTGCAG | AGCTTCATGC | TGCGGGGTGG | TGTTGTAGAT | GATCCAGTCG | 6180 |
| TAGCAGGAGC | GCTGGGCGTG | GTGCCTAAAA | ATGTCTTTCA | GTAGCAAGCT | GATTGCCAGG | 6240 |
| GGCAGGCCCT | TGGTGTAAGT | GTTTACAAAG | CGGTTAAGCT | GGGATGGGTG | CATACGTGGG | 6300 |
| GATATGAGAT | GCATCTTGGA | CTGTATTTTT | AGGTTGGCTA | TGTTCCCAGC | CATATCCCTC | 6360 |
| CGGGGATTCA | TGTTGTGCAG | AACCACCAGC | ACAGTGTATC | CGGTGCACTT | GGGAAATTTG | 6420 |
| TCATGTAGCT | TAGAAGGAAA | TGCGTGGAAG | AACTTGGAGA | CGCCCTTGTG | ACCTCCAAGA | 6480 |
| TTTTCCATGC | ATTCGTCCAT | AATGATGGCA | ATGGGCCAC | GGGCGGCGGC | CTGGGCGAAG | 6540 |
| ATATTTCTGG | GATCACTAAC | GTCATAGTTG | TGTTCCAGGA | TGAGATCGTC | ATAGGCCATT | 6600 |
| TTTACAAAGC | GCGGCGGAG | GGTGCCAGAC | TGCGGTATAA | TGGTTCCATC | CGGCCCAGGG | 6660 |
| GCGTAGTTAC | CCTCACAGAT | TTGCATTTCC | CACGCTTTGA | GTTCAGATGG | GGGGATCATG | 6720 |
| TCTACCTGCG | GGGCGATGAA | GAAAACGGTT | TCCGGGGTAG | GGGAGATCAG | CTGGGAAGAA | 6780 |
| AGCAGGTTCC | TGAGCAGCTG | CGACTTACCG | CAGCCGGTGG | GCCCGTAAAT | CACACCTATT | 6840 |
| ACCGGGTGCA | ACTGGTAGTT | AAGAGAGCTG | CAGCTGCCGT | CATCCCTGAG | CAGGGGGGCC | 6900 |
| ACTTCGTTAA | GCATGTCCCT | GACTCGCATG | TTTTCCCTGA | CCAAATCCGC | CAGAAGGCGC | 6960 |
| TCGCCGCCCA | GCGATAGCAG | TTCTTGCAAG | GAAGCAAAGT | TTTTCAACGG | TTTGAGACCG | 7020 |
| TCCGCCGTAG | GCATGCTTTT | GAGCGTTTGA | CCAAGCAGTT | CCAGGCGGTC | CCACAGCTCG | 7080 |
| GTCACCTGCT | CTACGGCATC | TCGATCCAGC | ATATCTCCTC | GTTTCGCGGG | TTGGGGCGGC | 7140 |
| TTTCGCTGTA | CGGCAGTAGT | CGGTGCTCGT | CCAGACGGGC | CAGGGTCATG | TCTTTCCACG | 7200 |
| GGCGCAGGGT | CCTCGTCAGC | GTAGTCTGGG | TCACGGTGAA | GGGGTGCGCT | CCGGGCTGCG | 7260 |
| CGCTGGCCAG | GGTGCGCTTG | AGGCTGGTCC | TGCTGGTGCT | GAAGCGCTGC | CGGTCTTCGC | 7320 |
| CCTGCGCGTC | GGCCAGGTAG | CATTTGACCA | TGGTGTCATA | GTCCAGCCCC | TCCGCGGCGT | 7380 |
| GGCCCTTGGC | GCGCAGCTTG | CCCTTGGAGG | AGGCGCCGCA | CGAGGGCAG | TGCAGACTTT | 7440 |
| TGAGGGCGTA | GAGCTTGGGC | GCGAGAAATA | CCGATTCCGG | GGAGTAGGCA | TCCGCGCCGC | 7500 |
| AGGCCCCGCA | GACGGTCTCG | CATTCCACGA | GCCAGGTGAG | CTCTGGCCGT | TCGGGGTCAA | 7560 |
| AAACCAGGTT | TCCCCCATGC | TTTTTGATGC | GTTTCTTACC | TCTGGTTTCC | ATGAGCCGGT | 7620 |

```
GTCCACGCTC  GGTGACGAAA  AGGCTGTCCG  TGTCCCCGTA  TACAGACTTG  AGAGGCCTGT   7680
CCTCGACCGA  TGCCCTTGAG  AGCCTTCAAC  CCAGTCAGCT  CCTTCCGGTG  GGCGCGGGGC   7740
ATGACTATCG  TCGCCGCACT  TATGACTGTC  TTCTTTATCA  TGCAACTCGT  AGGACAGGTG   7800
CCGGCAGCGC  TCTGGGTCAT  TTTCGGCGAG  GACCGCTTTC  GCTGGAGCGC  GACGATGATC   7860
GGCCTGTCGC  TTGCGGTATT  CGGAATCTTG  CACGCCCTCG  CTCAAGCCTT  CGTCACTGGT   7920
CCCGCCACCA  AACGTTTCGG  CGAGAAGCAG  GCCATTATCG  CCGGCATGGC  GGCCGACGCG   7980
CTGGGCTACG  TCTTGCTGGC  GTTCGCGACG  CGAGGCTGGA  TGGCCTTCCC  CATTATGATT   8040
CTTCTCGCTT  CCGGCGGCAT  CGGGATGCCC  GCGTTGCAGG  CCATGCTGTC  CAGGCAGGTA   8100
GATGACGACC  ATCAGGGACA  GCTTCAAGGA  TCGCTCGCGG  CTCTTACCAG  CCTAACTTCG   8160
ATCACTGGAC  CGCTGATCGT  CACGGCGATT  TATGCCGCCT  CGGCGAGCAC  ATGGAACGGG   8220
TTGGCATGGA  TTGTAGGCGC  CGCCCTATAC  CTTGTCTGCC  TCCCCGCGTT  GCGTCGCGGT   8280
GCATGGAGCC  GGGCCACCTC  GACCTGAATG  GAAGCCGGCG  GCACCTCGCT  AACGGATTCA   8340
CCACTCCAAG  AATTGGAGCC  AATCAATTCT  TGCGGAGAAC  TGTGAATGCG  CAAACCAACC   8400
CTTGGCAGAA  CATATCCATC  GCGTCCGCCA  TCTCCAGCAG  CCGCACGCGG  CGCATCTCGG   8460
GCAGCGTTGG  GTCCTGGCCA  CGGGTGCGCA  TGATCGTGCT  CCTGTCGTTG  AGGACCCGGC   8520
TAGGCTGGCG  GGGTTGCCTT  ACTGGTTAGC  AGAATGAATC  ACCGATACGC  GAGCGAACGT   8580
GAAGCGACTG  CTGCTGCAAA  ACGTCTGCGA  CCTGAGCAAC  AACATGAATG  GTCTTCGGTT   8640
TCCGTGTTTC  GTAAAGTCTG  GAAACGCGGA  AGTCAGCGCC  CTGCACCATT  ATGTTCCGGA   8700
TCTGCATCGC  AGGATGCTGC  TGGCTACCCT  GTGGAACACC  TACATCTGTA  TTAACGAAGC   8760
CTTTCTCAAT  GCTCACGCTG  TAGGTATCTC  AGTTCGGTGT  AGGTCGTTCG  CTCCAAGCTG   8820
GGCTGTGTGC  ACGAACCCCC  CGTTCAGCCC  GACCGCTGCG  CCTTATCCGG  TAACTATCGT   8880
CTTGAGTCCA  ACCCGGTAAG  ACACGACTTA  TCGCCACTGG  CAGCAGCCAC  TGGTAACAGG   8940
ATTAGCAGAG  CGAGGTATGT  AGGCGGTGCT  ACAGAGTTCT  TGAAGTGGTG  GCCTAACTAC   9000
GGCTACACTA  GAAGGACAGT  ATTTGGTATC  TGCGCTCTGC  TGAAGCCAGT  TACCTTCGGA   9060
AAAAGAGTTG  GTAGCTCTTG  ATCCGGCAAA  CAAACCACCG  CTGGTAGCGG  TGGTTTTTTT   9120
GTTTGCAAGC  AGCAGATTAC  GCGCAGAAAA  AAAGGATCTC  AAGAAGATCC  TTTGATCTTT   9180
TCTACGGGGT  CTGACGCTCA  GTGGAACGAA  AACTCACGTT  AAGGGATTTT  GGTCATGAGA   9240
TTATCAAAAA  GGATCTTCAC  CTAGATCCTT  TTAAATTAAA  AATGAAGTTT  TAAATCAATC   9300
TAAAGTATAT  ATGAGTAAAC  TTGGTCTGAC  AGTTACCAAT  GCTTAATCAG  TGAGGCACCT   9360
ATCTCAGCGA  TCTGTCTATT  TCGTTCATCC  ATAGTTGCCT  GACTCCCCGT  CGTGTAGATA   9420
ACTACGATAC  GGGAGGGCTT  ACCATCTGGC  CCCAGTGCTG  CAATGATACC  GCGAGACCCA   9480
CGCTCACCGG  CTCCAGATTT  ATCAGCAATA  AACCAGCCAG  CCGGAAGGGC  CGAGCGCAGA   9540
AGTGGTCCTG  CAACTTTATC  CGCCTCCATC  CAGTCTATTA  ATTGTTGCCG  GGAAGCTAGA   9600
GTAAGTAGTT  CGCCAGTTAA  TAGTTTGCGC  AACGTTGTTG  CCATTGCTGC  AGGCATCGTG   9660
GTGTCACGCT  CGTCGTTTGG  TATGGCTTCA  TTCAGCTCCG  GTTCCCAACG  ATCAAGGCGA   9720
GTTACATGAT  CCCCCATGTT  GTGCAAAAAA  GCGGTTAGCT  CCTTCGGTCC  TCCGATCGTT   9780
GTCAGAAGTA  AGTTGGCCGC  AGTGTTATCA  CTCATGGTTA  TGGCAGCACT  GCATAATTCT   9840
CTTACTGTCA  TGCCATCCGT  AAGATGCTTT  TCTGTGACTG  GTGAGTACTC  AACCAAGTCA   9900
TTCTGAGAAT  AGTGTATGCG  GCGACCGAGT  TGCTCTTGCC  CGGCGTCAAC  ACGGGATAAT   9960
ACCGCGCCAC  ATAGCAGAAC  TTTAAAAGTG  CTCATCATTG  GAAAACGTTC  TTCGGGGCGA  10020
```

| | | | | | | |
|---|---|---|---|---|---|---|
| AAACTCTCAA | GGATCTTACC | GCTGTTGAGA | TCCAGTTCGA | TGTAACCCAC | TCGTGCACCC | 10080 |
| AACTGATCTT | CAGCATCTTT | TACTTTCACC | AGCGTTTCTG | GGTGAGCAAA | AACAGGAAGG | 10140 |
| CAAAATGCCG | CAAAAAGGG | AATAAGGGCG | ACACGGAAAT | GTTGAATACT | CATACTCTTC | 10200 |
| CTTTTTCAAT | ATTATTGAAG | CATTTATCAG | GGTTATTGTC | TCATGAGCGG | ATACATATTT | 10260 |
| GAATGTATTT | AGAAAAATAA | ACAAATAGGG | GTTCCGCGCA | CATTTCCCCG | AAAAGTGCCA | 10320 |
| CCTGACGTCT | AAGAAACCAT | TATTATCATG | ACATTAACCT | ATAAAAATAG | GCGTATCACG | 10380 |
| AGGCCCTTTC | GTCTTCAA | | | | | 10398 |

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: other nucleic acid ( x i ) SEQUENCE DESCRIPTION: SEQ ID NO:2:

| | | |
|---|---|---|
| CATGGTAATA | GCGATGACTA | 20 |

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: other nucleic acid ( x i ) SEQUENCE DESCRIPTION: SEQ ID NO:3:

| | | |
|---|---|---|
| GCTCTGCTTA | TATAGACCTC | 20 |

METHOD FOR EXPRESSING A GENE IN THE ABSENCE OF AN IMMUNE RESPONSE

This work was supported by the National Institutes of Health Grant No. DK47757. The U.S. Government has certain rights in this invention.

BACKGROUND OF THE INVENTION

Adeno-associated virus (AAV) is a replication-deficient parvovirus, the genome of which is about 4.6 kb in length, including 145 nucleotide inverted terminal repeats (ITRs). The single-stranded DNA genome of AAV contains genes responsible for replication (rep) and formation of virions (cap).

When this nonpathogenic human virus infects a human cell, the viral genome integrates into chromosome 19 resulting in latent infection of the cell. Production of infectious virus and replication of the virus does not occur unless the cell is coinfected with a lytic helper virus such as adenovirus or herpesvirus. Upon infection with a helper virus, the AAV provirus is rescued and amplified, and both AAV and helper virus are produced.

AAV possesses unique features that make it attractive as a vector for delivering foreign DNA to cells. Various groups have studied the potential use of AAV in the treatment of disease states. However, the performance of rAAV as a vector for in vivo models of gene therapy has been mixed.

What is needed is a method of improving rAAV-mediated gene transfer.

SUMMARY OF THE INVENTION

The present invention provides a method of improving expression of a selected gene delivered to an animal via recombinant AAV gene therapy. The method involves introducing a recombinant AAV vector comprising a desired transgene into the muscle of the animal. Preferably, the vector is administered into cardiac, skeletal, or smooth muscle.

In one preferred embodiment, the rAAV-delivered transgene delivered encodes a secretable protein which is therapeutically useful. In another embodiment, the transgene encodes a non-secretable protein (e.g., a dystrophin gene) for which delivery to the muscle is desired (e.g., for treatment of muscular dystrophy).

In another aspect, the present invention provides a method of treating an animal with hemophilia. The method involves administering into the muscle of the animal a recombinant adeno-associated virus comprising the gene for factor IX and sequences which regulate expression of the gene.

In yet another aspect, the invention provides a method of treating an animal with atherosclerosis. The method involves administering into the muscle of the animal a recombinant adeno-associated virus comprising the gene for ApoE and regulatory sequences capable of expressing said gene.

Other aspects and advantages of the present invention are described further in the following detailed description of the preferred embodiments thereof.

BRIEF DESCRIPTION OF THE DRAWINGS

FIG. 4A shows the predicted PCR product assuming a direct end-to-end tandem ligation of monomer AV.CMVLacZ genomes. Two complete ITRs (shaded box) with their respective "FLOP" and "FLIP" orientation are shown at the junction (labeled j). The CMV promoter (solid black box) and polyadenylation signal (open box) are also indicated.

DETAILED DESCRIPTION OF THE INVENTION

Figure 1:
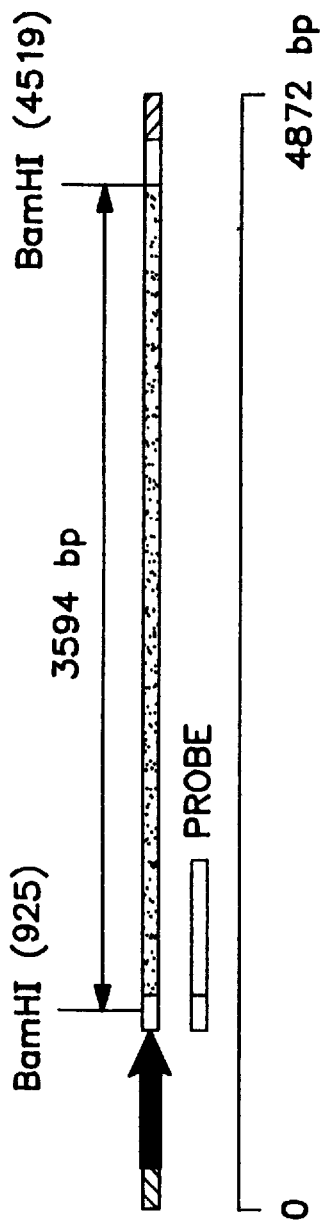
FIG. 1 is a schematic illustration showing the linear arrangement of AV.CMVLacZ (4872 bp). The relevant elements include AAV ITRs (solid black boxes), CMV promoter (hatched arrow), SV40 intron and polyadenylation signal (open boxes), and lacZ DNA (shaded box).

The present invention provides a method for adeno-associated virus (AAV) mediated gene therapy which provides high level and stable transgene expression as compared to prior art methods. Particularly, this method involves introducing a recombinant AAV carrying a desired transgene into an animal's muscle. Desirably, the rAAV vector is injected directly into cardiac, skeletal, or smooth muscle and the transgene is a secreted therapeutic protein. However, the method of the invention is similarly useful for administration of non-secreted, therapeutically useful genes.

Particularly, the inventors have demonstrated that intramuscular injection of purified rAAV (i.e., rAAV which is substantially free of contamination with adenovirus or wild-type AAV) leads to efficient transduction of postmitotic muscle fibers with the provirus integrating into chromosomal DNA leading to very prolonged transgene expression. According to the invention, this is accomplished without significant inflammation or activation of immunity to the transgene product, despite the fact that the product may be a neoantigen, which in the context of adenovirus is extremely immunogenic.

The stability of transgene expression produced according to the methods of this invention is particularly impressive. Without wishing to be bound by theory, this stability is believed to be due to integration of proviral DNA. Several observations support this hypothesis. As described in the examples below, analysis of Hirt extracts failed to detect a double-stranded episomal form of the viral genome. Southern analysis of total cellular DNA revealed a discrete band when digested with an enzyme that has two sites within the vector, whereas no band is observed when the same DNA was digested with an enzyme that does not have sites within the viral genome.

Further DNA analysis focused on the formation of contatamers and their structure. Previous studies of lytic AAV infections have shown that the episomal replication of rAAV proceeds through head-to-head or tail-to-tail contatamers, while latent infections that result in proviral integration are established as head-to-tail tandem arrays. In contrast, the data set forth herein demonstrates the production of contatamers consisting exclusively of head-to-tail tandem arrays.

Sequence analysis of the junctions indicated consistent but variable deletions of both ITRs. Fluorescent in situ hybridization (FISH) analysis was consistent with single integration sites in approximately 1 in 20 nuclei, while Southern analysis indicated an average of 1 proviral genome per diploid genome of the muscle fiber. Together these findings indicate that integration of the AAV vector occurs in a minority of nuclei as contatamers of approximately 5 proviral genomes in length. This presumes that FISH detects all integrations.

Another advantage of the method of the invention is the relative absence of inflammation upon administration of therapeutic doses of vector. Furthermore, C57BL/6 mice injected with a lacZ AAV vector failed to mount a humoral immune response to *E.coli* β-galactosidase despite the fact that vibrant anti-β-galactosidase antibodies were elicited in these animals when a lacZ adenovirus was injected into skeletal muscle. Thus, the AAV vector, when injected into muscle, is able to modulate immune responses to the transgene. This contrasts sharply with prior art methods, such as naked plasmid DNA or adenovirus-mediated gene therapy, which elicit strong immune responses. Thus, the method of the invention provides a significant advantage over other vector systems, particularly with respect to the treatment of chronic disorders.

I. The Recombinant AAV

A recombinant AAV vector carrying a selected transgene is used in the methods of the invention. In addition to the transgene, the vector further contains regulatory sequences which control expression of the transgene in a host cell, e.g., a muscle cell.

Many rAAV vectors are known to those of skill in the art and the invention is not limited to any particular rAAV vector. For example, suitable AAV vectors and methods of producing same are described in U.S. Pat. No. 5,252,479; U.S. Pat. No. 5,139,941; International Patent Application No. W094/13788; and International Patent Application No. W093/24641, which are incorporated by reference herein. One particularly desired vector is described below.

A. The AAV Sequences

Currently, a preferred rAAV is deleted of all viral open reading frames (ORFs) and retains only the cis-acting 5' and 3' inverted terminal repeat (ITR) sequences [See, e.g., B. J. Carter, in "Handbook of Parvoviruses", ed., P. Tijsser, CRC Press, pp.155–168 (1990)]. Thus, the rep and cap polypeptide encoding sequences are deleted. The AAV ITR sequences are about 143 bp in length. While it is preferred that substantially the entire 5' and 3' sequences encoding the ITRs are used in the vectors, some degree of minor modification of these sequences is permissible. The ability to modify these ITR sequences is within the skill of the art. See, e.g., texts such as Sambrook et al, "Molecular Cloning. A Laboratory Manual.", 2d edit., Cold Spring Harbor Laboratory, New York (1989).

The AAV ITR sequences may be obtained from any known AAV, including presently identified human AAV types. The selection of the AAV is not anticipated to limit the invention. A variety of AAV strains, types 1–4, are available from the American Type Culture Collection or available by request from a variety of commercial and institutional sources. Similarly, AAVs known to infect other animals may also be employed in the vector constructs of this invention. In the examples set forth herein, an AAV-2 is used for convenience. Specifically, the 5' and 3' AAV ITR sequences flank a selected transgene sequence and associated regulatory elements, described below.

B. The Transgene

The transgene sequence contained within the rAAV vector is a nucleic acid sequence, heterologous to the AAV sequence, which encodes a polypeptide or protein of interest. The transgene is operatively linked to regulatory components in a manner which permits transgene expression.

The composition of the transgene sequence will depend upon the use to which the resulting vector will be put. For example, one type of transgene sequence includes a reporter sequence, which upon expression produces a detectable signal. Such reporter sequences include without limitation an *E. coli* beta-galactosidase (LacZ) cDNA, an alkaline phosphatase gene and a green fluorescent protein gene. These sequences, when associated with regulatory elements which drive their expression, provide signals detectable by conventional means, e.g., ultraviolet wavelength absorbance, visible color change, etc.

A more preferred transgene sequence includes a therapeutic gene which encodes a desired gene product in a host cell. These therapeutic nucleic acid sequences typically encode products which, when administered to a patient in vivo or ex vivo, are able to replace or correct an inherited or non-inherited genetic defect or treat an epigenetic disorder or disease.

The method of the invention, which delivers the transgene to the muscle cells, is particularly well suited for use in connection with secreted therapeutic proteins, such as factor IX, useful in treatment of hemophilia, or apolipoprotein (Apo) E, useful in treatment of atherosclerosis. However, other therapeutic genes, particularly those which are secreted, may be readily selected by the skilled artisan. Examples of genes encoding secreted protein include, without limitation, those encoding β-interferon (β-IFN), erythropoietin (epo), insulin, growth hormone (GH), and parathyroid hormone (PTH). These genes are useful for treatment of a variety of conditions, including multiple sclerosis and cancer (β-IFN), anemia (epo), diabetes (insulin), small stature (GH), and osteoporosis (PTH). The method of the invention is also useful for delivery of non-secreted proteins to the muscle. For example, the method of the invention is anticipated to be useful in treatment of muscular dystrophies, by enabling delivery of a dystrophin gene [see, e.g., C. C. Lee et al, *Nature*, 349:334–336 (1991)] via a rAAV according to the method of the invention. The selection of the transgene is not considered to be a limitation of this invention, as such selection is within the knowledge of the skilled artisan.

C. Regulatory Elements of the Vector

In addition to the AAV ITR sequences and the transgene, the vector also includes conventional regulatory elements necessary to drive expression of the transgene in a cell transfected with the vector. Thus the vector desirably contains a selected promoter/enhancer which is linked to the transgene and located, with the transgene, between the AAV ITR sequences of the vector.

Selection of the promoter is a routine matter and is not a limitation of the vector itself. Useful promoters may be constitutive promoters or regulated (inducible) promoters, which will control expression of the transgene. For example, a desirable promoter is that of the cytomegalovirus immediate early promoter/enhancer [see, e.g., Boshart et al, Cell, 41:521–530 (1985)]. Another desirable promoter include, without limitation, the Rous sarcoma virus LTR promoter/enhancer and the inducible mouse metallothienien promoter. Still other promoter/enhancer sequences may be selected by one of skill in the art.

The vectors will also desirably contain nucleic acid sequences heterologous to the AAV sequences including sequences providing signals required for efficient polyadenylation of the transcript and introns with functional splice donor and acceptor sites. A common poly-A sequence which is employed in the exemplary vectors of this invention is that derived from the papovavirus SV-40. The poly-A sequence generally is inserted in the vector following the transgene sequences and before the 340 AAV ITR sequence. A common intron sequence is also derived from SV-40, and is referred to as the SV-40 T intron sequence. A rAAV vector of the present invention may also contain such an intron, desirably located between the promoter/enhancer sequence and the transgene. Selection of these and other elements desirable to control or enhance gene expression are conventional and many such sequences are known to those of skill in the art [see, e.g., Sambrook et al, and references cited therein].

The combination of the transgene, promoter/enhancer and the other regulatory elements are referred to as a "minigene" for ease of reference herein. As above stated, the minigene is flanked by the 5' and 3' AAV ITR sequences. Provided with the teachings of this invention, the design of such a minigene can be made by resort to conventional techniques.

An example of a rAAV, i.e., AV.CMVLacZ, useful in the method the invention is provided in the examples below. As set forth in FIG. 1, this exemplary rAAV contains a 5'AAV ITR, a CMV promoter, an SV-40 intron, a LacZ transgene, an SV-40 poly-A sequence and a 3'AAV ITR. However, as stated above, the method is not limited to use of any particular rAAV.

D. Production of rAAV

The material from which the sequences used in the rAAV vector are derived and the various vector components and sequences employed in the construction of the rAAV of this invention may be obtained from commercial or academic sources based on previously published and described materials. These materials may also be obtained from an individual patient or generated and selected using standard recombinant molecular cloning techniques known and practiced by those skilled in the art. Any modification of existing nucleic acid sequences using in the production of the rAAV vectors, including sequence deletions, insertions, and other mutations are also generated using standard techniques.

Assembly of the rAAV, including the sequences of AAV, the transgene and other vector elements, may be accomplished using conventional techniques. One particularly desirable technique is described in K. J. Fisher et al, *J. Virol.*, 70(1):520–532 (January, 1996), which is incorporated by reference herein. However, other suitable techniques include cDNA cloning such as those described in texts [Sambrook et al, cited above], use of overlapping oligonucleotide sequences of the AAV genome, polymerase chain reaction, and any suitable method which provides the desired nucleotide sequence. Where appropriate, standard transfection and co-transfection techniques are employed, e.g., CaPO$_4$ transfection techniques using the complementation human embryonic kidney (HEK) 293 cell line (a human kidney cell line containing a functional adenovirus E1a gene which provides a transacting E1a protein) or another suitable cell line, which may be readily selected by the skilled artisan. Other conventional methods employed in this invention include homologous recombination of the viral genomes, plaquing of viruses in agar overlay, methods of measuring signal generation, and the like.

Desirably, the rAAV produced are purified using conventional techniques to remove any contaminating adenovirus or wild-type AAV. A particularly desirable purification scheme is described in K. J. Fisher et al, *J. Virol.*, 70(1):520–532 (January, 1996), which is incorporated by reference. However, one of skill in the art can readily select other appropriate purification means.

II. Therapeutic Applications

Once a rAAV containing a desired transgene is obtained, the vector is administered directly into an animal's muscle. One advantage of the method of the invention is that muscle is particularly well suited as a site for production of secreted therapeutic protein, such as factor IX or apolipoprotein (Apo) E, among others. Alternatively, the method of the invention is used to deliver a non-secreted gene product.

The rAAV viruses of the present invention may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The rAAV vectors of this invention are administered in sufficient amounts to provide sufficient levels of integration and expression of the selected transgene such that a therapeutic benefit may be obtained without undue adverse effects and with medically acceptable physiological effects which can be determined by those skilled in the medical arts. In a preferred embodiment, the rAAV are injected directly into cardiac, skeletal, or smooth muscle. However, other suitable methods of administration include intravenous and intraarterial means.

Dosages of the rAAV vector will depend primarily on factors such as the condition being treated, the selected transgene, the age, weight and health of the patient, and may thus vary among patients. A therapeutically effective dose of the rAAV of the present invention is believed to be in the range of from about 1 to about 50 ml of saline solution containing concentrations of from about $1 \times 10^8$ to $1 \times 10^{11}$ particles/ml rAAV vector of the present invention. A more preferred human dosage is about 1–20 ml saline solution at the above concentrations. The levels of expression of the selected gene can be monitored to determine the selection, adjustment or frequency of administration. Administration of the rAAV may be repeated as needed.

The examples set forth below illustrate the preferred methods for preparing the vectors and performing the methods of the invention. These examples are illustrative only and do not limit the scope of the invention.

EXAMPLE 1

Production of AV.CMVLacZ

A recombinant AAV, AV.CMVLacZ, was constructed in which the AAV rep and cap genes were replaced with a minigene expressing β-galactosidase from a CMV promoter. With reference to FIG. 1, the linear arrangement of AV.CMVLacZ includes:

(a) the 5' AAV ITR (bp 1–173) obtained by PCR using pAV2 [C. A. Laughlin et al, *Gene*, 23: 65–73 (1983)] as template [nucleotide numbers 365–538 of SEQ ID NO: 1];

(b) a CMV immediate early enhancer/promoter [Boshart et al, *Cell*, 41:521–530 (1985); nucleotide numbers 563–1157 of SEQ ID NO: 1], (c) an SV40 intron (nucleotide numbers 1178–1179 of SEQ ID NO: 1), (d) an *E. coli* beta-galactosidase CDNA (nucleotide numbers 1356–4827 of SEQ ID NO: 1), (e) an SV40 polyadenylation signal (a 237 Bam HI-BclI restriction fragment containing the cleavage/poly-A signals from both the early and late transcription units; nucleotide numbers 4839–5037 of SEQ ID NO: 1) and (f) the 3' AAV ITR, obtained from pAV2 as a SnaBI-BglII fragment (nucleotide numbers 5053–5221 of SEQ ID NO: 1).

Two Bam HI sites are present in the double-stranded vector sequence. The first is located in the SV40 intron at bp position 925 and the second lies between the lacZ DNA and the SV40 polyadenylation signal at bp position 4519. Therefore, digestion of the double-stranded sequence with BamHI releases a fragment of 3594 bp in length. The location of a cDNA probe that can be used to detect the internal BamHI fragment, as well as full-length vector, is also shown.

This plasmid was purified using standard techniques [see, e.g., K. F. Kozarsky et al, *J. Biol. Chem.*, 269:13695–13702 (1994)] for use in the following experiments.

EXAMPLE 1A rAAV production and purification

As described in K. J. Fisher et al, (Jan. 1996), cited above, lots of the AV.CMV.LacZ vector may be produced for use in the method of the invention as set forth in the following steps.

Monolayers of 293 cells (certified AAV free; Human Applications Laboratory, University of Pennsylvania, Philadelphia) grown to 90% confluency in 150-mm-diameter culture dishes ($5 \times 10^7$ cells per plate; 90 plates total) were infected with H5.CBALP at a multiplicity of infection (MOI) of 10. Infections were done in Dulbecco's modified Eagle medium (DMEM) supplemented with 2% fetal bovine serum (FBS) at 20 ml of medium per 150-mm-diameter plate. At 2 h postinfection, 50 µg of plasmid DNA (37.5 µg of trans-acting DNA and 12.5 µg of cis-acting DNA) was added to each plate as a calcium phosphate precipitate and evenly distributed. Cells were left in this condition for 10 to 14 h, after which the infection-transfection medium was replaced with 20 ml of fresh DMEM-2% FBS. Following transfection, (~50 h), cells were harvested and suspended in 10 mM Tris-Cl (pH 8.0) buffer (45-ml final volume) and a lysate was prepared by sonication. The lysate was brought to 10 mM manganese chloride, after which bovine pancreatic DNase I (20,000 U) and RNase (0.2-mg/ml final concentration) were added and the reaction mixture was incubated at 37° C. for 30 min. Sodium deoxycholate was added to a final concentration of 1%, and the mixture was incubated at 37° C. for an additional 10 min. The treated lysate was chilled on ice for 10 min, and solid CsCl was added to a final density of 1.3 g/ml. The lysate was brought to a final volume of 60 ml with a 1.3-g/ml CsCl solution in 10 mM Tris-Ci (pH 8.0) and divided into three equal aliquots. Each 20-ml sample was layered onto a CsCl step gradient composed of two 9.0-ml tiers with densities of 1.45 and 1.60 g/ml. Centrifugation was performed at 25,000 rpm in a Beckman SW-28 rotor for 24 h at 4° C. One-milliliter fractions were collected from the bottom of the tube and analyzed on 293 or 293(E4) cells for lacZ transduction. Fractions containing peak titers of the functional AV.CMV.LacZ vector were combined and subjected to three sequential rounds of equilibrium sedimentation in CsCl. The rotors used included Beckman NVT-90 (80,000 rpm for 4 h) and SW-41 (35,000 rpm 20 h) rotors. At equilibrium, AV.CMV.LacZ appeared as an opalescent band at 1.40 to 1.41 g/ml of CsCl. Densities were calculated from refractive index measurements. The purified vector was transferred to 20 mM N-2-hydroxyethylpiperazine-N'-2-ethanesulfonic acid (HEPES) buffer (pH 7,8) containing 150 mM NaCl by dialysis and stored frozen at −80° C. in the presence of 10% glycerol or as a liquid stock at −20° C. in 20 mM HEPES buffer (pH 7.8)-150 mM NaCl-40% glycerol.

EXAMPLE 2 rAAV Stably Transduces Skeletal Muscle in Vivo

A highly purified preparation of lacZ rAAV was injected into skeletal muscle of adult C57BL/6 mice in the presence of an E2a deleted adenovirus to enhance transduction.

Briefly, purified AV.CMVLacZ ($1 \times 10^9$ genomes in 25 µl PBS) was injected into the tibialis anterior of 5 week old C57BL/6 mice and tissue was harvested at days 3, 17, 30, 64, and 180 post-injection. Samples of AV.CMVLacZ ($1 \times 10^9$ genomes in 25 µl PBS) were also supplemented with an adenovirus E2a mutant dl802 [S. A. Rice and D. L. Klessig, *J. Virol.*, 56:767–778 (1985)] ($5 \times 10^{10}$ $A_{260}$ particles, $1 \times 10^8$ pfu) just prior to injection. Tissue from animals that received the AV.CMVLacZ+dl802 mixture were harvested on days 3 and 17 post-injection. Cryosections were cut, stained for β-galactosidase, counterstained with neutral red, and mounted.

Analysis of tissue by X-gal histochemistry revealed high level transduction of muscle fibers by day 17 associated with substantial inflammation. Surprisingly, animals that received rAAV in the absence of adenovirus demonstrated levels of transduction that exceeded those found in the presence of adenovirus. These high levels have persisted without apparent diminution for 180 days.

EXAMPLE 3 rAAV Genome Integrates with High Efficiency as Truncated Head-to-Tail Contatamers In order to characterize the molecular state of the stabilized rAAV genome, skeletal muscle was harvested from mice injected as above. Models in which the rAAV genome persists either as an episomal double-stranded genome such as those formed during lytic infection, or as an integrated provirus resembling latent infection, were considered.

A. Detection of Episomal Double-Stranded Genome

To detect nonintegrated forms of the rAAV genome, Hirt extracts of muscle DNA were analyzed by hybridization with a $^{32}$P-labeled cDNA that maps to the probe sequence shown in FIG. 1. The Hirt DNA samples (15 µl, equivalent to 15 mg tissue) were extracted from muscle harvested on day 8, 17, 30, and 64 post-injection. The marker lanes contained Hirt DNA that was extracted from cultured cells infected with AV.CMVLacZ and stimulated with adenovirus E1 and E4 genes. Under these conditions, the single-stranded AV.CMVLacZ genome is converted to a duplex DNA. This model simulates the second-strand synthesis reaction that is necessary for rAAV transduction.

Analysis of cells infected with rAAV in the presence of adenovirus revealed both the single-stranded and monomeric double-stranded forms of the virus. Similar studies of Hirt extracts of transduced muscle demonstrated the single-stranded genome by day 8 that diminished to undetectable levels by day 64. Double-stranded forms of AAV were never detected even when the filters were over-exposed. These studies indicate that the single-stranded rAAV genome is efficiently transferred into cells of skeletal muscle; however, it is not converted to transcriptionally active episomal forms.

B. Detection of Integrated Proviral DNA

To detect integrated proviral DNA, additional hybridization studies were performed with total cellular DNA harvested from transduced skeletal muscle 64 days post-infection. Genomic DNA (10 µg, equivalent to 18 µg tissue) restricted with HindIII, a restriction enzyme that does not cut proviral DNA, resulted in a smear after gel fractionation and hybridization to a virus specific probe. This contrasts with the result obtained with genomic DNA digested with BamHI, a restriction enzyme that cuts twice within the provirus. A discrete band of the predicted size of 3.6 kb was detected at an abundance of approximately 1 proviral genome/diploid host cell genome.

The structure of the integrated provirus was further characterized to further delineate its structure potential mechanisms of persistence. Previous studies of wild type and rAAV have suggested different pathways of DNA replication in the lytic and latent phases of the viral life cycle. In the presence of helper virus, AAV replicates to form dimeric replicative intermediates by a mechanism that results in the synthesis of head-to-head or tail-to-tail contatamers. This contrasts with latent infections where the integrated proviral genome is characterized by head-to-tail genomic arrays.

C. PCR Analysis

Genomic DNA from skeletal muscle was subjected to PCR analysis to amplify junctions between AAV genomic contatamers. A PCR method was developed to detect integrated AV.CMVLacZ, based on data indicate integrated forms of rAAV are typically found as head-to-tail concatomers.

Figure 2A:
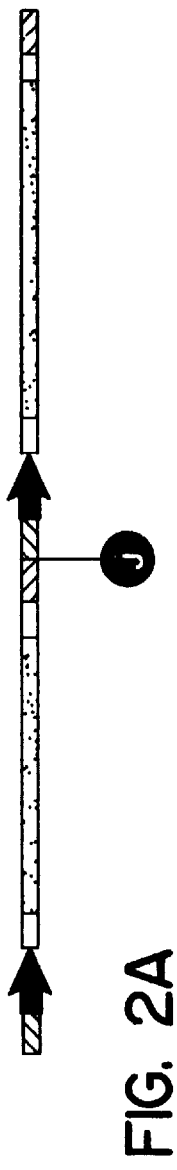
FIG. 2A is a schematic illustration of the linear arrangement of AV.CMVLacZ concatomer. The relevant landmarks include AAV ITRs (hatched boxes), CMV enhancer/promoter (solid black arrow), SV40 intron and polyadenylation signal (open boxes), and lacZ CDNA (shaded box). AAV.CMVLacZ monomer is shown joined according to a direct end-to-end ligation mechanism (labeled j) at the ITRs. Therefore, in the cartoon two copies of the AAV ITR are present at the junction.
Figure 2B:
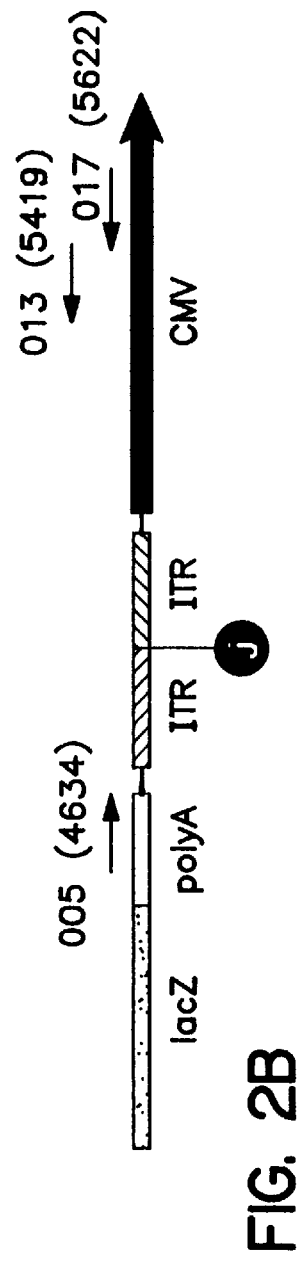
FIG. 2B is a schematic illustration showing an amplified view of the junction domain. Relevant landmarks are as indicated in FIG. 2A above. Horizontal arrows indicate the location and direction of PCR primers used to amplify across the provirus junction. Primer 005 is a sense-strand primer. Primers 013 and 017 are antisense-strand primers.

No amplification products were detected when primers were used that should span a head-to-head or tail-to-tail junction (data not shown). Junctions between head-to-tail contatamers (FIG. 2A) was studied by PCR using oligonucleotides to the SV40 polyA and CMV promoter (FIG. 2B). If the ITRs are retained intact, oligos 005+013 [SEQ ID NO: 2: CATGGTAATAGCGATGACTA] should amplify a 796 bp fragment while oligos 005 and 017 [SEQ ID NO: 3: GCTCTGCTTATATAGACCTC] should amplify a 1000 bp fragment. It is important to emphasize that the predicted PCR product sizes are based on the assumption that provirus junctions contain two ITR copies. Amplification across a junction that has fewer than two copies will therefore generate a PCR product that is proportionally smaller in size.

PCR reactions were conducted on genomic DNA isolated from AV.CMVLacZ transduced muscle harvested at day 64 post-infection, as described above. Genomic DNA from muscle injected with Hepes buffered saline (HBS) was used as a negative PCR control. PCR reactions were also conducted with genomic DNA from cell lines that contain integrated AV.CMVLacZ. The provirus structure of these clones has been determined by Southern blot analysis. Three cell lines (10-3.AV5, 10-3.AV6, and 10-3.AV18) each of which contain at least two monomer copies of integrated AV.CMVLacZ arranged head-to-tail were identified. Based on the size of the PCR products, two clones (a 720 bp product using primer set 005–013, and a 930 bp product using primer set 005–017) likely contain 1.5 copies of AAV ITR at the junction, while another clone (a 320 bp product using primer set 005–013, 500 bp product using primer set 005–017) contains a large deletion that encompasses the AAV ITRs. Another cell line contains a single monomer copy of integrated AV.CMVLacZ according to Southern blotting, and appears to be confirmed by the absence of a PCR product.

Thus, analysis of DNA from cell lines derived from an in vitro infection with the lacZ AAV revealed distinct bands representing head-to-tail junctions in which one or both of the ITRs have been deleted. Analysis of DNA from skeletal muscle revealed a smear following agarose gel electrophoresis consistent with a heterogeneous population of head-to-tail contatamers.

D. Structural Analysis

Detailed structural analyses of the proviral junctions recovered from skeletal muscle DNA was performed by subcloning from the PCR reaction (FIG. 3) followed by sequence analysis (FIGS. 4A–G). Particularly, PCR products from one of the samples obtained as described above (FIG. 2) were directly ligated into plasmid pCRII (Invitrogen). Competent bacterial strain Topp1 [Stratagene] were transformed with the ligation reactions and plated under selection. In effect, this procedure results in a plasmid library of PCR products. The library was screened by overlaying developed colonies with a nylon membrane and hybridizing with a $^{32}$P-labeled fragment corresponding to the CMV promoter. Colonies that scored positive were picked and small-scale cultures grown.

Figure 3:
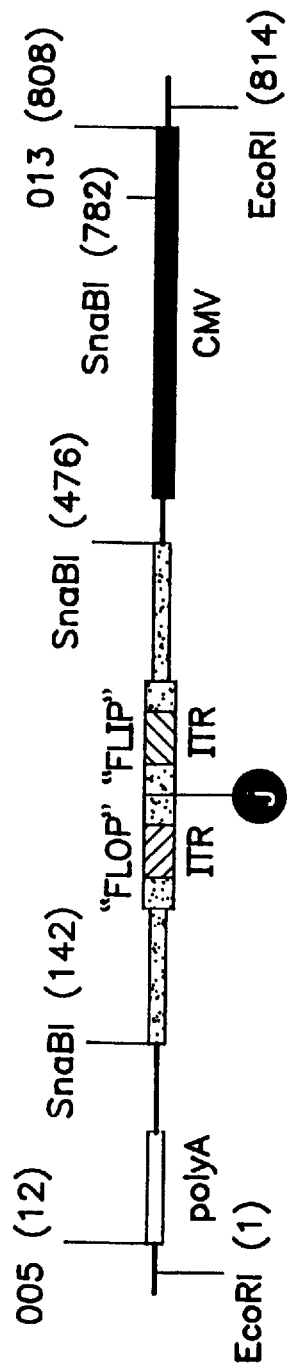
FIG. 3 is a schematic illustration showing the predicted PCR product assuming a direct end-to-end tandem ligation of monomer AV.CMVLacZ genomes. Two complete ITRs (shaded box) with their respective "FLOP" and "FLIP" orientation are shown at the junction (labeled j). The CMV promoter (solid black box) and polyadenylation signal (open box) are also indicated. The PCR cloning site in pCRII is flanked by EcoRI sites as shown. The location of three SnaBI sites positioned within the PCR product are also shown. Primers 005 and 013 also indicated.
Figure 4A:
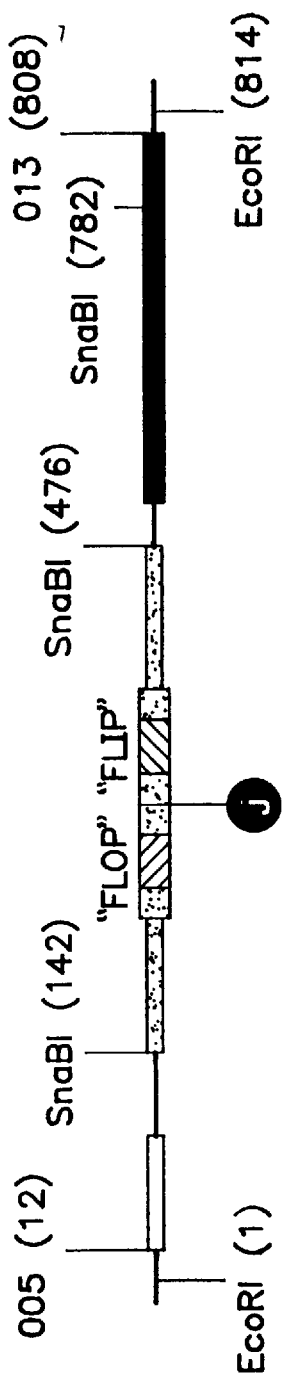
FIG. 4A, in conjunction with FIGS. 4B–4G, illustrates the structure of PCR products that map to the head-to-tail junction of AV.CMVLacZ concatomers of FIG. 3.
Figure 4B:
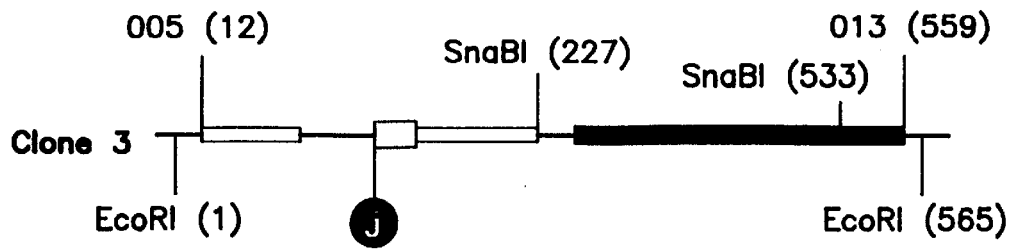
FIG. 4B illustrates the structure of the PCR product from Clone 3.
Figure 4C:
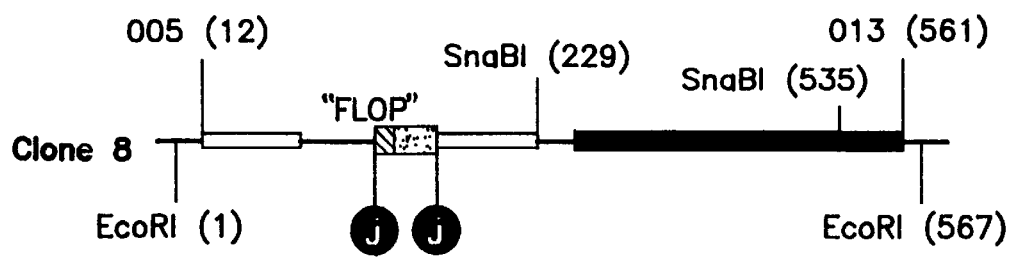
FIG. 4C illustrates the structure of the PCR product from Clone 8. Clone 8 is nearly identical in size to clone 3, but contains a different rearrangement of the ITR junction.
Figure 4D:
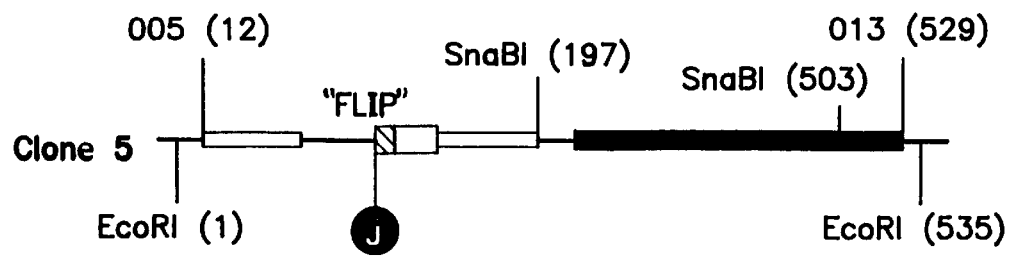
FIG. 4D illustrates the structure of the PCR product from Clone 5.
Figure 4E:
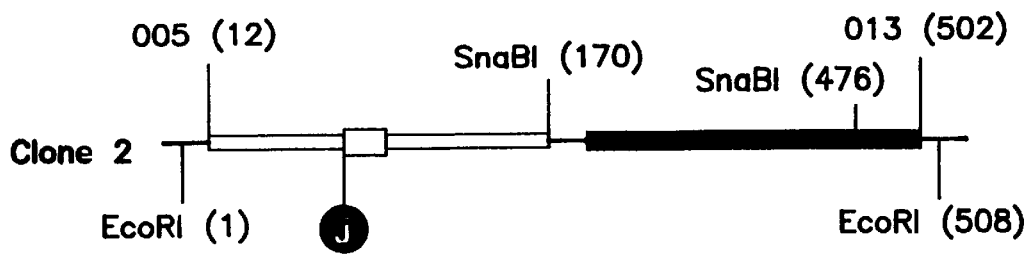
FIG. 4E illustrates the structure of the PCR product from Clone 2.
Figure 4F:
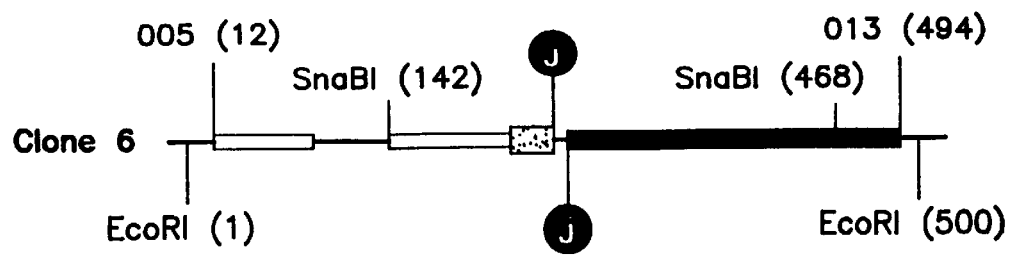
FIG. 4F illustrates the structure of the PCR product from Clone 6.
Figure 4G:
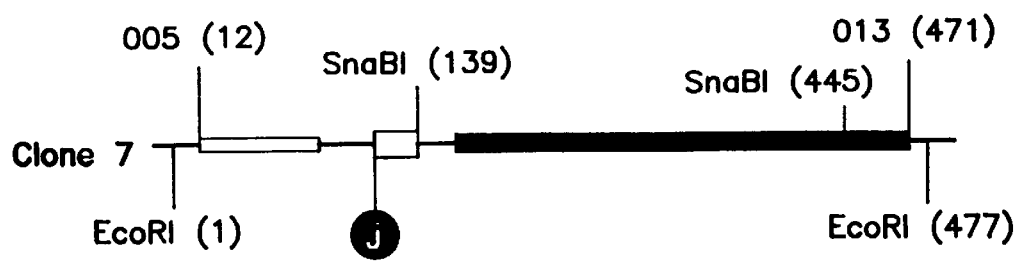
FIG. 4G illustrates the structure of the PCR product from Clone 7.

Plasmid DNA was extracted from overnight small-scale cultures and digested with either EcoRI to release the entire PCR product or with SnaBI as a diagnostic indicator (see FIG. 3). Digestion with SnaBI should release a 306 bp fragment (SnaBI 476 to SnaBI 782) spanning the CMV promoter. The release of a second fragment mapping to the ITR junction (SnaBI 142 to SnaBI 476) is contingent on rearrangements that occur during formation of the concatomer, and could therefore range in size from 334 bp (2 complete ITR copies) to 0 bp if the ITRs have been deleted. The PCR product from one of the cell lines believed to contain 1.5 copies of AAV ITR (10-3.AV5) was also cloned into PCRII and digested with the indicated enzyme. This sample serves as a positive control for the diagnostic SnaBI digestion.

Digestion of this sample with EcoRI correctly releases the 730 bp PCR fragment, as well as a secondary doublet band approximately 500 bp in size. This secondary band is believed to be an artifact due to secondary structure that develops in the 1.5 copies of AAV ITR during replication in bacteria. Digestion of the positive control with SnaBI releases the diagnostic 306 bp fragment from the CMV promoter and a 250 bp fragment that maps to the ITR junction.

Digestion of individual clones with EcoRI and SnaBI indicated deletions of variable lengths were present in all recovered junctions and largely confined to ITRs at the junctions. Sequence analyses further indicated that most deletions spanned portions of both ITRs at the junctions without involving contiguous viral DNA.

E. FISH Analysis

FISH was performed on cryosections of skeletal muscle to characterize the distribution of proviral DNA within the injected tissue. Serial sections were alternatively stained for β-galactosidase activity to identify transgene expressing muscle fibers and hybridized with a biotinylated proviral probe to localize the distribution of the proviral genome.

More particularly, muscle sections from mice injected with AV.CMVLacZ and harvested on day 180 were hybridized with digoxigenin (DIG)-labeled sequence of the rAAV genome. Localization was performed with an anti-DIG-RITC conjugated antibody. Sections were counterstained with 4'-6'-diamidino-2-phenylindole (DAAP) for nuclear imaging. Analysis of tissue injected with lacZ virus revealed discrete foci of hybridization within the peripherally located nuclei of muscle fibers. No signal of this type was detected in muscle tissue from animals not injected with virus. Signal was detected in approximately 5% of nuclei contained within X-gal positive fibers; positive nuclei usually contained only a single hybridizing focus.

EXAMPLE 4 rAAV Blunts Transgene Directed Immune Responses

The stability of lacZ expression achieved with rAAV was surprising in light of previous work with adenoviral vectors which demonstrated destructive immune responses to β-galactosidase expressing muscle fibers. Transgene specific immune responses were studied by measuring sera for the formation of β-galactosidase antibodies using Western analysis. Intramuscular injection of an E1 deleted adenovirus into skeletal muscle of C57BL/6 mice yielded substantial β-galactosidase and, therefore, should be immune tolerant to the product of the vector derived lacZ gene. No C57BL/6 or lacZ transgenic animals developed antibodies to β-galactosidase after intramuscular injection with lacZ AAV.

EXAMPLE 5

Comparative Studies of Ad vs. AAV Vectors

Studies of the biology of muscle-directed gene transfer mediated by recombinant AAV and adenovirus demonstrate that adenoviruses, but not AAV, infect antigen presenting cells (APCs), which elicit a cascade of immunological responses leading to destructive cellular and humoral immunity.

An experimental paradigm was constructed to define the specific differences in host responses to skeletal muscle-directed gene transfer with recombinant AAV and adenovirus. The goal was to delineate differences in the biology of these vector systems that lead to preferential immunologic activation directed against a transgene product (i.e., β-galactosidase) when expressed from a recombinant adenoviral vector, but not an AAV vector.

The general approach was to inject a lacZ expressing AAV into the right leg of a mouse. This has been shown in the examples above to confer efficient and stable gene expression. In other experimental groups, the animals receive rAAV in addition to various combinations of vectors and cells in order to define components of the immune response to Ad that leads to destructive cellular and humoral immunity. The effect of these experimental manipulations are followed by assessing their impact on the stability of the AAV engrafted muscle fibers, as well as measuring other immunologic parameters. Any intervention that elicits immunity to β-gal muscle fibers can be detected by assessing the stability of transgene expression in the AAV transduced muscle, and the development of inflammation.

Four experimental groups were developed for this study as summarized below. Virus was injected into mice using techniques substantially similar to those described in Example 2 above, i.e., virus was suspended in phosphate-buffered saline and injected directly into the tibialia anterior muscles. When the animals were necropsied, muscle tissues were snap-frozen in liquid nitrogen-cooled isopentane and sectioned at 6 μm thickness, while serum samples and the draining inguinal lymph nodes were harvested for immunological assays.

Figure 5B:
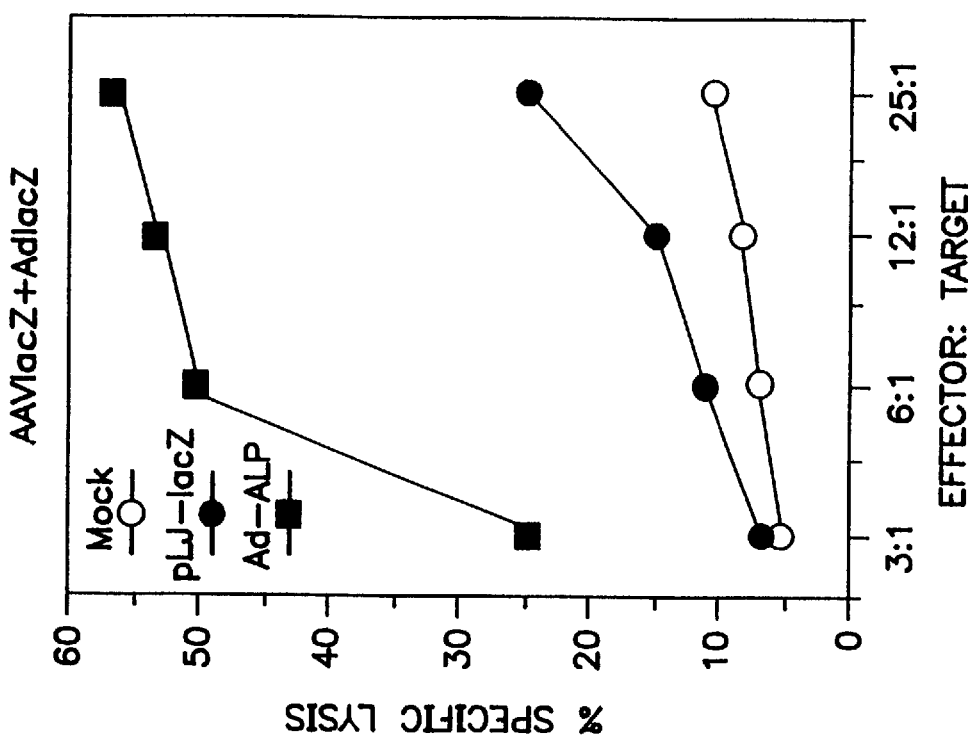
FIG. 5B characterizes the activation of cytotoxic T lymphocytes directed against adenoviral antigen as well as lacZ. This is an analysis of lymphocytes harvested from Group 2 of Example 5.
Figure 5A:
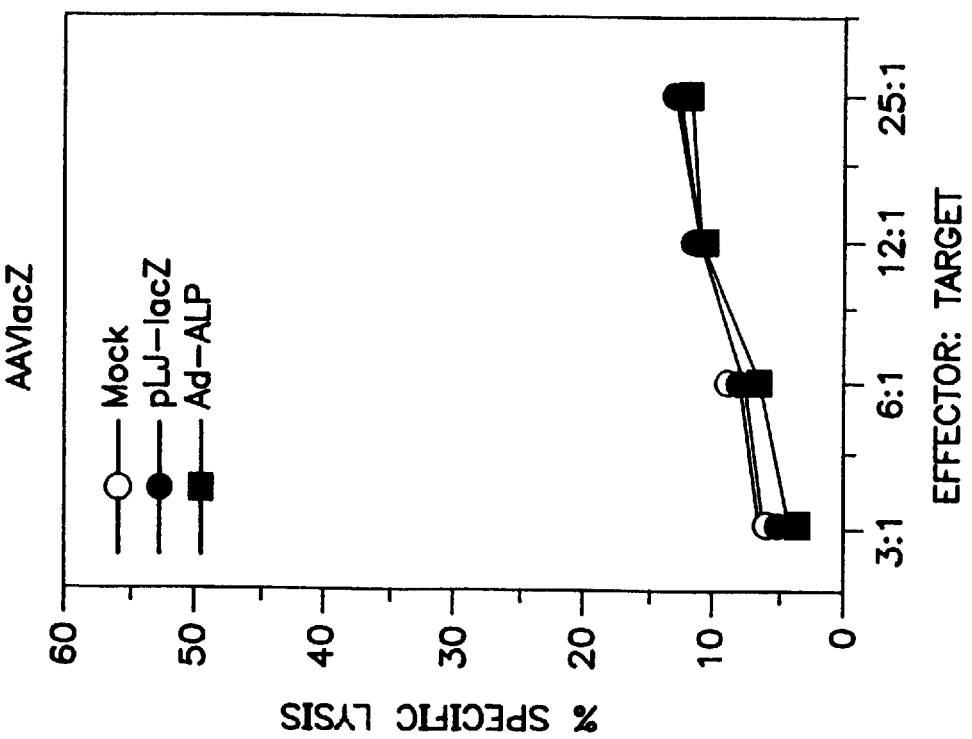
FIG. 5A characterizes the activation of cytotoxic T lymphocytes directed against adenoviral antigen as well as lacZ. This is an analysis of lymphocytes harvested from Group 1 of Example 5.
Figure 5C:
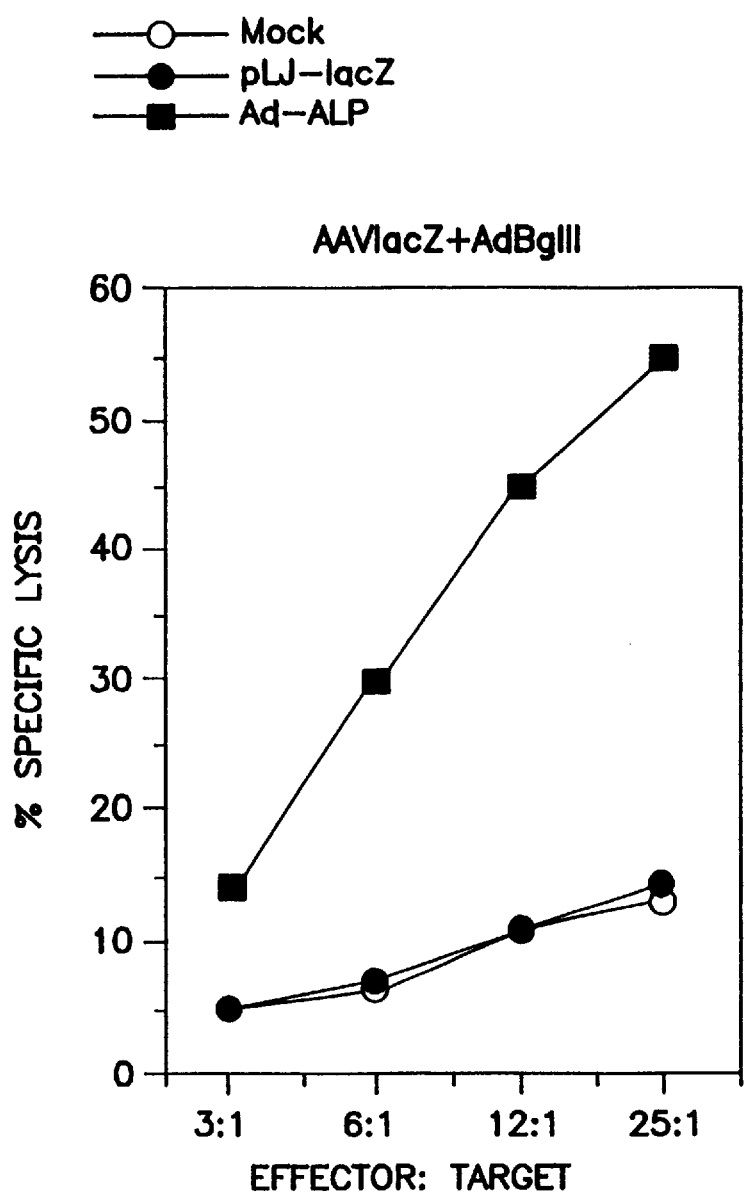
FIG. 5C characterizes the activation of cytotoxic T lymphocytes directed against adenoviral antigen as well as lacZ. This is an analysis of lymphocytes harvested from Group 3 of Example 5.

Lymphocytes were harvested from inguinal lymph nodes and a standard 6 hr $^{51}$chromium (Cr)-release assay was performed essentially as described below, using different ratios of effector to target cells (C57SV, H-2$^b$) in 200 μl DMEM in V-bottom 96-well plates. Prior to mixing with the effector cells, target cells were either infected with an adenovirus expressing alkaline phosphatase (AdALP) or stably transduced with a lacZ-expressing retrovirus, pLJ-lacZ, labeled with 100 μCi of $^{51}$Cr and used at 5×10$^3$ cells/well. After incubation for 6 hr, aliquots of 100 μl supernatant were counted in a gamma counter. The results for groups 1–3 are provided in FIGS. 5A–5C.

Frozen sections (6 μm) were fixed in methanol and stained with anti-CD4 and anti-CD8 antibodies. Morphometric analysis was performed to quantify the number of CD8+ cell and CD4+ cells per section.

Figure 6A:
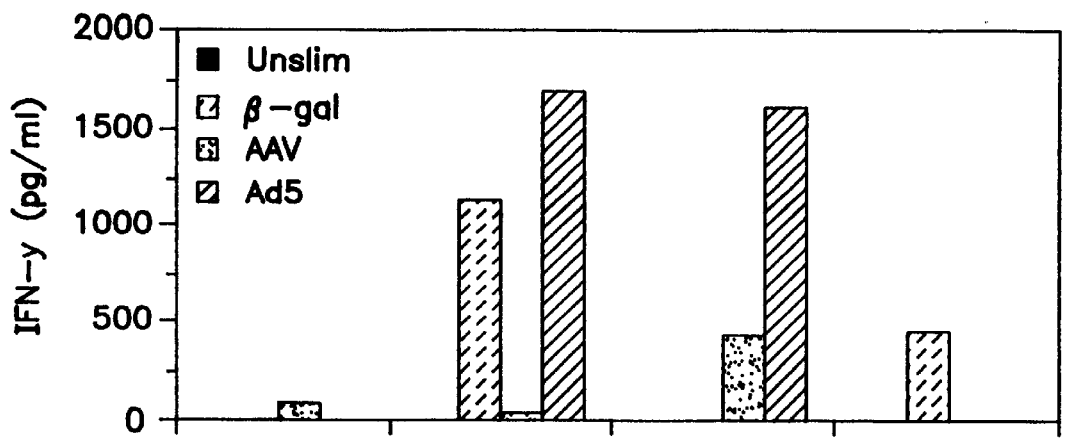
FIG. 6A shows the activation of T lymphocytes in response to different antigens including β-galactosidase, purified AAV, or adenovirus, for each of Groups 1–4 of Example 5. Activation is demonstrated by the secretion of IFN-γ representing the TH1 subset of T cells.
Figure 6B:
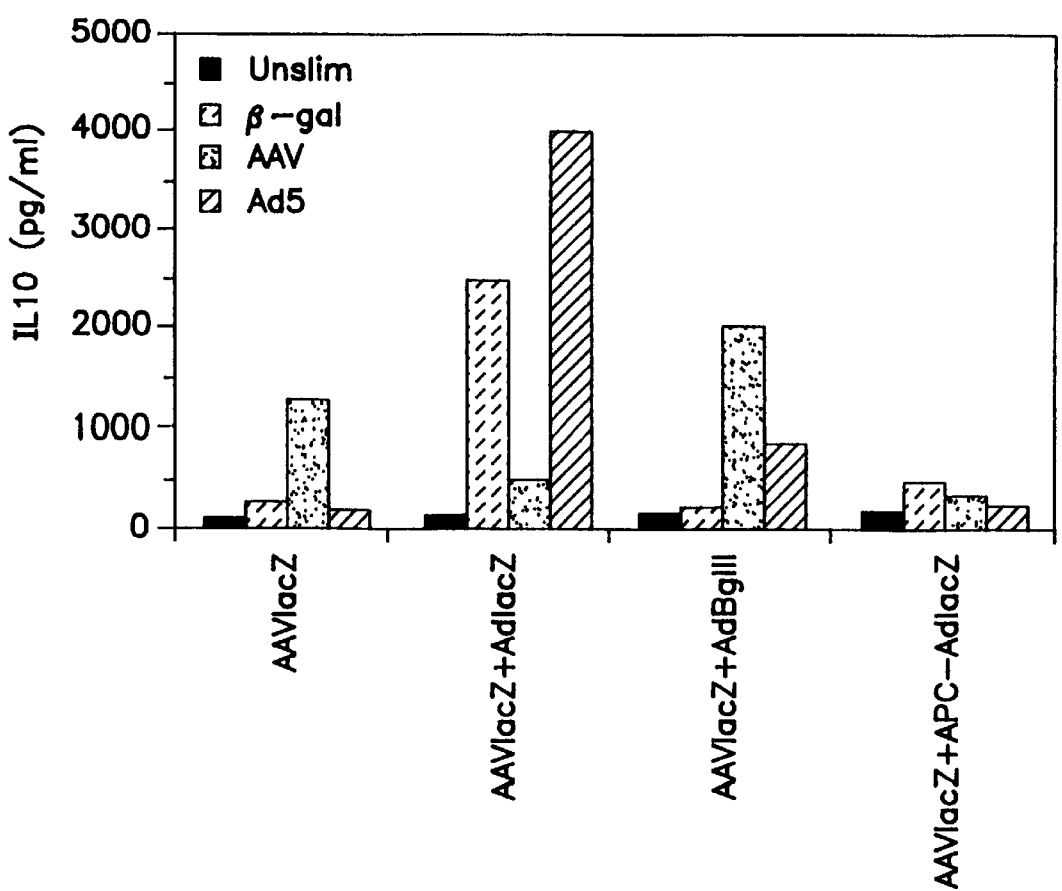
FIG. 6B shows the activation of T lymphocytes in response to different antigens including β-galactosidase, purified AAV, or adenovirus, for each of Groups 1–4 of Example 5. Activation is demonstrated by the secretion of IL-10 representing the TH2 subset of T cells.

The cytokine release assay was performed essentially as follows. Lymphocytes were restimulated for 40 hr with β-galactosidase, purified AAV, or adenovirus type 5. Cell-free supernatants (100 μl) were assayed for the secretion of IL10 and IFN-γ. Proliferation was measured 72 hr later by a 8 hr ³H-thymidine (0.50 μCi/well) pulse. The results for the four groups is provided in FIGS. 6A and 6B.

The neutralizing antibody assay was performed essentially as follows. Mouse serum samples were incubated at 56° C. for 30 min to inactivate complement and then diluted in DMEM in twofold steps starting from 1:20. Each serum dilution (100 μl) was mixed with β-galactosidase or adenovirus type 5. After 60 min incubation at 37° C., 100 μl of DMEM containing 20% FBS was added to each well. Cells were fixed and stained for β-galactosidase expression in the following day. All of the cells stained blue in the absence of serum samples. The results for the four groups is provided in FIGS. 7A and 7B.

Figure 7A:
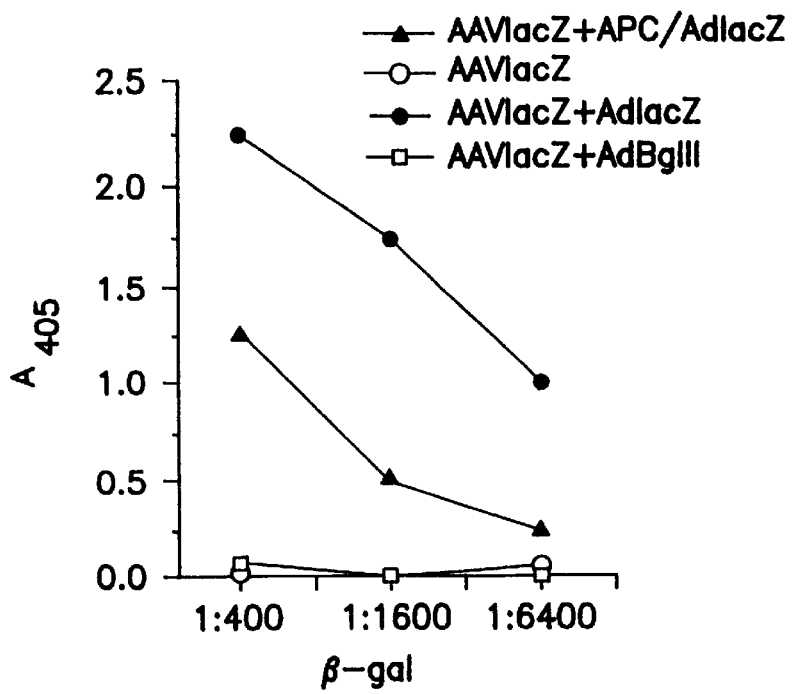
FIG. 7A illustrates results from an enzyme linked immunosorbent assay (ELISA), showing the development of antibodies directed against β-galactosidase in the various groups of example 5.
Figure 7B:
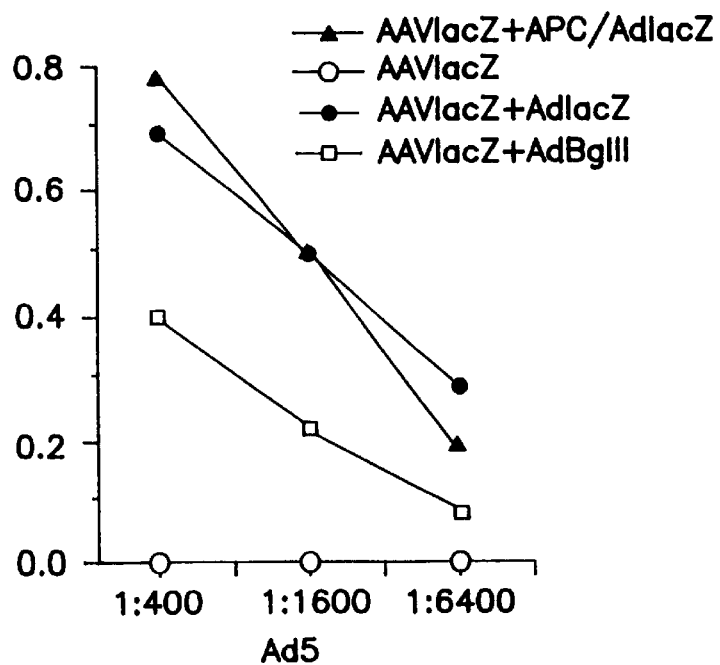
FIG. 7B illustrates results from an enzyme linked immunosorbent assay (ELISA), showing the development of antibodies directed against adenovirus type 5 in the various groups of example 5.

Group 1 mice received AV.CMVlacZ, produced as described in Example 1, in the right leg and no other intervention. Transduction with AV.CMVlacZ alone led to high level and stable gene transfer (evident even at 28 days) without infiltration of lymphocytes. No activation of CD8 T cells was detected (FIG. 5). Nor were CD4 T cells to any antigens [i.e., viral or β-galactosidase (FIGS. 6A and 6B)] detected. Antibodies were not generated to β-galactosidase or adenovirus (FIGS. 7A and 7B).

Group 2 mice received AV.CMVlacZ in the right leg and adenovirus expressing lacZ in the left leg. The goal of this group was to determine if the immunologic response to the Ad-infected fibers was systemic as demonstrated by its impact on the biology of the contralateral AAV lacZ transduced leg. Apparently, the adenoviral lacZ treatment induced immunity to β-galactosidase that led to the destruction of the AAV lacZ transduced fibers. Not surprisingly, this was associated with infiltration of both CD4 and CD8 T cells into the AAV transduced leg, and the activation of cytotoxic T lymphocytes to both adenoviral and β-galactosidase antigens (FIG. 5). CD4 T cells were activated to AAV, Ad, and β-gal antigens (FIG. 6) and antibodies generated to adenovirus and β-galactosidase were also observed (FIG. 7).

Group 3 animals received a mixture of AV.CMVlacZ and Ad BglII in the right leg. AdBglII is an E1 deleted adenovirus that expresses no recombinant gene. The goal of this group was to determine if the adenovirus provides an adjuvant effect which would elicit immunity to AAV encoded lacZ in this setting. This did not lead to loss of transgene expression, although there was substantial infiltration of CD8 and some activation of CD4 T cells to viral antigens, but not to β-galactosidase (FIG. 6). As expected, antibodies were generated to adenovirus but not to β-galactosidase (FIG. 7).

Group 4 animals received AV.CMVlacZ in the right leg and were adoptively transferred with antigen presenting cells harvested from naive animals and infected ex vivo with adenovirus.

These animals mounted a vigorous and effective immunologic response to β-gal, as demonstrated by the loss of transgene expression, and the massive infiltration of CD8 and CD4 T cells. CD4 T cells were activated to β-gal in this experiment as shown in FIG. 6, and antibodies generated, as shown in FIG. 7.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

---

What is claimed is:

1. A method for transducing a skeletal muscle cell with a transgene encoding a protein of interest in the absence of a cytotoxic immune response directed against said cell, comprising the step of introducing into said cell a recombinant adeno-associated virus (rAAV) which is substantially free of contamination with a helper virus, wherein said rAAV comprises said transgene operably linked to sequences which control its expression and wherein said transgene is expressed at detectable levels in said cell in the absence of a cytotoxic immune response directed against said cell.

2. The method according to claim 1 wherein said protein of interest is a secreted protein.

3. The method according to claim 2 wherein said secreted protein is selected from the group consisting of Factor IX, ApoE, β-interferon, insulin, erythropoietin, growth hormone, and parathyroid hormone.

4. The method according to claim 1 wherein said rAAV consists essentially of, from 5' to 3', a 5' AAV ITR sequence, a heterologous promoter, said transgene, a polyadenylation sequence, and 3' AAV ITR sequence.

\* \* \* \* \*